United States Patent
Tooke et al.

(12)

(10) Patent No.: US 6,852,851 B1
(45) Date of Patent: Feb. 8, 2005

(54) DNA ISOLATION METHOD

(75) Inventors: Nigel Eric Tooke, Knivsta (SE); Philip Landeg Thomas, Cardiff (GB); Michael Kenneth Kenrick, Caerphilly (GB)

(73) Assignee: Gyros AB, Uppsala (SE)

( * ) Notice: Subject to any disclaimer, the term of this patent is extended or adjusted under 35 U.S.C. 154(b) by 0 days.

(21) Appl. No.: 10/111,822

(22) PCT Filed: Oct. 20, 2000

(86) PCT No.: PCT/GB00/04047
§ 371 (c)(1),
(2), (4) Date: Aug. 16, 2002

(87) PCT Pub. No.: WO01/30995
PCT Pub. Date: May 3, 2001

(30) Foreign Application Priority Data

Oct. 28, 1999 (GB) .............................. 9925468

(51) Int. Cl.⁷ .............................................. C07H 21/04
(52) U.S. Cl. ................. 536/25.4; 435/306.1; 435/317.1
(58) Field of Search ......................... 435/306.1, 317.1; 536/25.4

(56) References Cited

U.S. PATENT DOCUMENTS 5,447,864 A * 9/1995 Raybuck et al. ............ 435/270
5,593,838 A    1/1997 Zanzucchi et al.
5,637,469 A    6/1997 Wilding et al.

FOREIGN PATENT DOCUMENTS

| EP | 0 693 560 A3 | 1/1996 |
|---|---|---|
| EP | 0 693 560 A2 | 1/1996 |
| WO | WO 97/21090 | 6/1997 |
| WO | WO 99/09042 | 2/1999 |
| WO | WO 99/55827 | 11/1999 |
| WO | WO 00/78455 A1 | 12/2000 |

* cited by examiner

*Primary Examiner*—James Ketter
(74) *Attorney, Agent, or Firm*—Fulbright & Jaworski, LLP

(57) ABSTRACT

Disclosed is a method and apparatus for the isolation of DNA or cell nuclei or a mixture thereof from cell samples in a CD device. The method includes treating a suspension of whole cells with a lysis reagent so as to lyse the cytoplasmic membrane and at least some of the nuclear membranes, and introducing the lysate into micro-channels of a microfabricated apparatus in which each of the micro-channels is provided with a barrier disposed in the channel to impede the passage or flow of DNA and cell nuclei each while allowing the passage of liquid through the micro-channel so that a mesh comprising DNA is formed in the channel.

16 Claims, 3 Drawing Sheets

DNA ISOLATION METHOD

The present invention relates to the isolation of DNA from cell samples, particularly mammalian blood, in a microfabricated apparatus, particularly in a CD device, prior to further analysis, for example DNA probing, amplification and sequencing.

BACKGROUND OF THE INVENTION

There is a requirement to isolate DNA rapidly and conveniently from a variety of cellular sources, including blood. The availability of DNA has greatly facilitated the analysis and characterisation of the genome in many organisms through the application of sequencing and hybridisation techniques. Conventional approaches to DNA isolation and purification are based on multi-step procedures involving phenol/chloroform (see for example Sambrook, J. et al, Molecular Cloning: A Laboratory Manual, $2^{nd}$ Edition, Cold Spring harbor Laboratory Press, 1989). These processes are inherently laborious, may result in damaged DNA samples and are generally not amenable to automation. A number of non-toxic extraction procedures have been reported (Nucleic Acids Research, 15, 859, 1987; Analytical Biochemistry, 120, 282–288 1982), but these require either extensive dialysis or use of filters. Improved extraction methods include the use of chaotropic agents (BioTechniques, 22, 550–553, 1997). Others may be applicable to specific cell types and involve only lysis, dilution and addition to a PCR tube (BioTechniques, 11, 30–31, 1991).

U.S. Pat. No. 5,650,506 (Becton Dickinson) relates to modified glass fiber membranes which exhibit sufficient hydrophilicity and electropositivity to bind DNA from a suspension containing DNA and permit elution of the DNA from the membrane. The modified glass fiber membranes are useful for purification of DNA from other cellular components. A product is also available based on isolation of DNA from blood on glass filters (GFX™ Genomic Blood DNA Purification Kit, Amersham Pharmacia Biotech).

U.S. Pat. Nos. 5,705,628 and 5,898,071 disclose a method for separating polynucleotides, such as DNA, RNA and PNA, from a solution containing polynucleotides by reversibly and non-specifically binding the polynucleotides to a solid surface, such as a magnetic microparticle. A similar approach has been used in a product, "Dynabeads DNA Direct" marketed by Dynal A/S, Norway.

U.S. Pat. No. 5,447,864 discloses a method of separating cell nuclei from cells by means of a pipette tip device, open at one end and having a membrane extending across its forward end. The method comprises treating a fluid containing whole cells so as to selectively lyse the cytoplasmic membrane, together with a small proportion of the nuclear membranes, but leaving a large proportion of the cell nuclei intact. The treated fluid is applied to the membrane whereby a mesh of DNA from the lysed nuclei is formed on the surface and captures intact cell nuclei. The mesh comprising DNA on the surface is then washed to separate the captured cell nuclei from other components of the cells. A device for use in the method is also described, the device comprising a pipette tip having a membrane that extends across its forward end.

Methods for the isolation of DNA in microstructured devices have demanded substantial simplification of conventional techniques that are time-consuming and frequently require centrifugation, pipetting, vortexing or thermal incubation steps. One approach to the purification of DNA from whole blood is to isolate the white blood cells prior to direct PCR (Nucleic Acids Research, 24, 380–385, 1996), thus removing a primary inhibitor of PCR, namely haemoglobin. Another approach (Science, 282, 399–401, 1998) involves mixing blood with a salt solution that lyses the cells. The lysate is then introduced into a chamber containing a glass wall on which DNA binds by charge interaction, while the rest of the sample is ejected. The DNA is washed with ethanol/water mixes and then eluted to a neighbouring chamber.

WO 97/21090 relates to methods and apparatus for performing micro-analytic and micro-synthetic procedures. The invention provides an apparatus comprising a rotatable disc which includes sample inlet port, fluid micro-channels, reaction chambers and outlet ports. Movement of fluids within the device, for example reagents, samples and other liquid components, is facilitated by rotation of the disc causing centripetal acceleration of the fluids through the micro-channels embedded in the disc. Methods specific for the apparatus are provided for performing a variety of procedures, including DNA synthesis, micro-extraction and cell counting.

A method for the extraction and concentration of short (500 bp) and medium size (48000 bp) DNA from test samples of bacteriophage lambda DNA utilising silicon fluidic microchips is disclosed in J.Biomechanical Engineering, 121, 23–27 (1999). PCR and gel electrophoresis were used to analyse the nucleic acid obtained by this process.

BRIEF SUMMARY OF THE INVENTION

The serial nature of the procedures for DNA isolation described above limits throughput. Moreover, such procedures are not readily amenable to automation. Sample preparation has consistently been demonstrated as the rate-limiting step in procedures which require the input of genomic DNA. The present invention relates to the isolation of DNA in a format which permits multiple cell samples to be processed in parallel. The complex sequential extraction processes of conventional methods of DNA isolation are performed seamlessly in parallel using microfluidics, in contrast with multi-channel and microwell pipetting procedures where each well must be accessed individually to add or remove reagents.

Accordingly, the present invention provides a method of isolating DNA and/or cell nuclei in a microfabricated apparatus that contains a plurality of micro-channels the method comprising forming a mesh in one or more of the micro-channels that acts as a barrier to DNA and/or cell nuclei.

Preferably the mesh formed in the said one or more micro-channels of the microfabricated apparatus comprises a mesh of nucleic acid.

In one aspect of the invention, there is provided a method of isolating DNA or cell nuclei or a mixture thereof from calls, which method comprises:
a) treating a suspension of whole cells with a lysis reagent so as to lyse the cytoplasmic membranes and at least some of the nuclear membranes;
b) introducing the lysate from step a) into micro-channels of a microfabricated apparatus wherein each of said micro-channels incorporates means to impede the passage or flow of DNA and cell nuclei while allowing the passage of liquid through the micro-channel whereby a mesh comprising DNA is formed in the channel; and,
c) washing the mesh comprising DNA.

Where it is desired to isolate cell nuclei, suitably step a) should be performed wherein a proportion of the nuclear membranes is left intact.

In another aspect of the present invention there is provided microfabricated apparatus for isolating DNA or cell nuclei or a mixture thereof from cells, which apparatus comprises a rotatable disc, the disc comprising a sample introduction port located towards the centre of the disc in contact with an annular sample reservoir which in turn is connected to a plurality of radially dispersed micro-channels, each micro-channel comprising an inlet channel and an outlet channel disposed towards the circumferential edge of the disc and means incorporated in each of the micro-channels to impede the passage or flow of DNA and cell nuclei, while allowing the passage of liquid therethrough.

Suitably, the means incorporated in each of the micro-channels to impede the passage or flow of DNA and cell nuclei comprises a barrier.

In one preferred embodiment of the present invention, the barrier comprises beads that impede the flow or passage of DNA and cell nuclei in the micro-channel, while allowing the passage of liquid. In a second preferred embodiment of the present invention, the barrier comprises raised structures disposed in the micro-channel. Preferably, the raised structures are moulded, for example to form pillars. In a particularly preferred embodiment of the invention, the raised structures are disposed on the base portion of the micro-channel and are moulded to form pillars such that they impede the flow or passage of DNA and cell nuclei in the micro-channel, while allowing the passage of liquid.

The method of the present invention may be used for the isolation of DNA or cell nuclei from any suitable nucleated cell source, for example from plant cells and animal cells. The invention is particularly suitable for the isolation of mammalian cell DNA, more particularly DNA from whole blood. Suitably, step a) of the method may be performed in a separate vessel prior to introduction of the cell lysate into the micro-channels of the microfabricated apparatus. Alternatively, step a) may be performed within the microfabricated apparatus, for example by treating the suspension of whole cells contained within the annular sample reservoir with the lysis reagent, prior to introduction of the lysate into the micro-channels of the apparatus.

Beads employed in the method of the invention may be of any suitable composition, for example plastics materials. Suitable plastics may be porous or non-porous, depending upon the degree of cross-linking in the polymer and they include polystyrene, styrene acrylate co-polymer, polystyrene cross-linked with divinylbenzene, polyvinyltoluene, polymethacrylate and polycarbonate. Alternative materials include polysaccharides (such as dextrani, metal oxides (such as aluminium oxide), glass and carbon. Optionally, the surface of the beads may be treated or activated by chemical or by physical means, for example by derivatisation with positively charged species, so as to render the surface more susceptible to binding by DNA.

Preferably at least some of the micro-channels of the microfabricated apparatus each further comprise a reaction chamber for performing assays or processing DNA and being connected in-line downstream of the barrier.

BRIEF DESCRIPTION OF THE DRAWINGS

In order that the invention may be better understood, the embodiments will now be described by way of example only and with reference to the accompanying drawings in which.

DETAILED DESCRIPTION OF THE INVENTION

Figure 1:
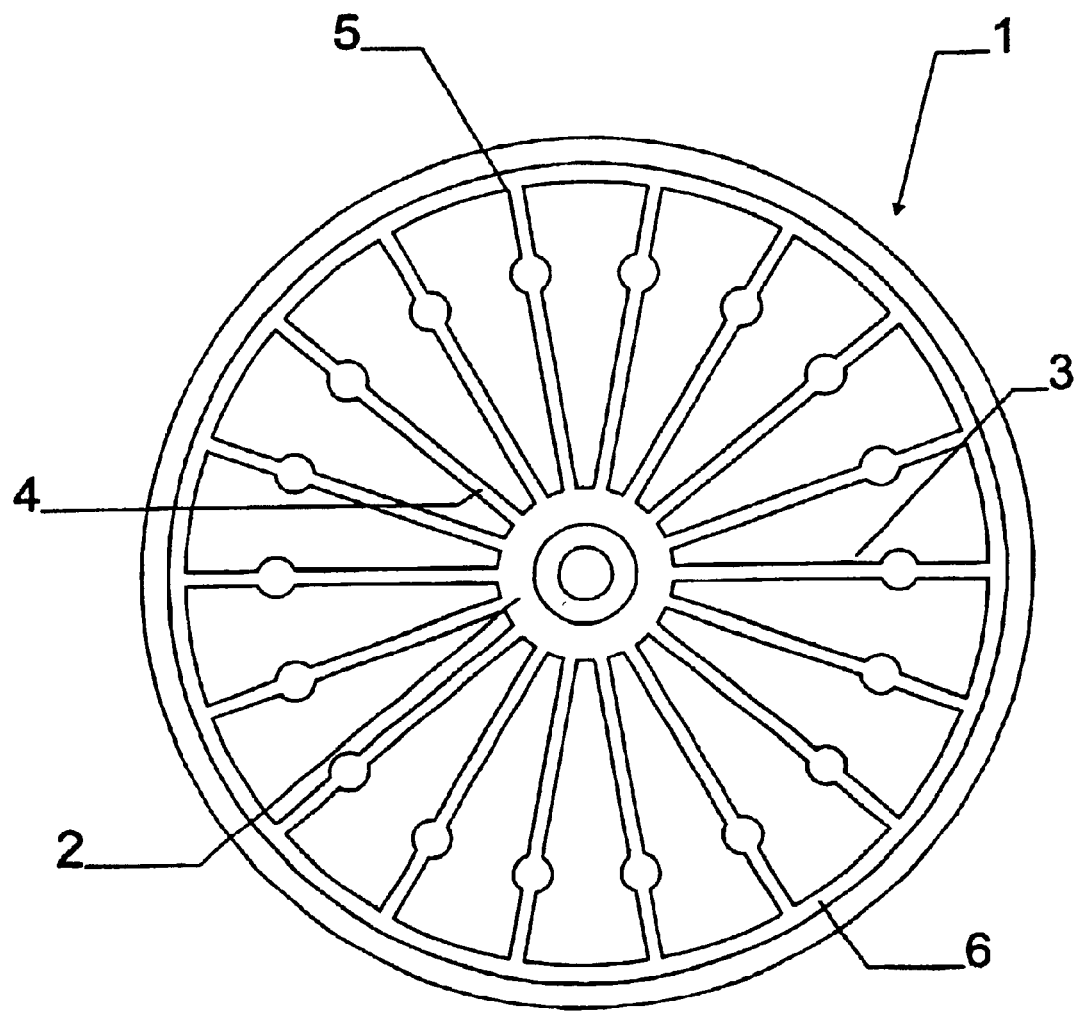
FIG. 1 is a plan view of a microfabricated disc for performing DNA isolation.
Figure 2:
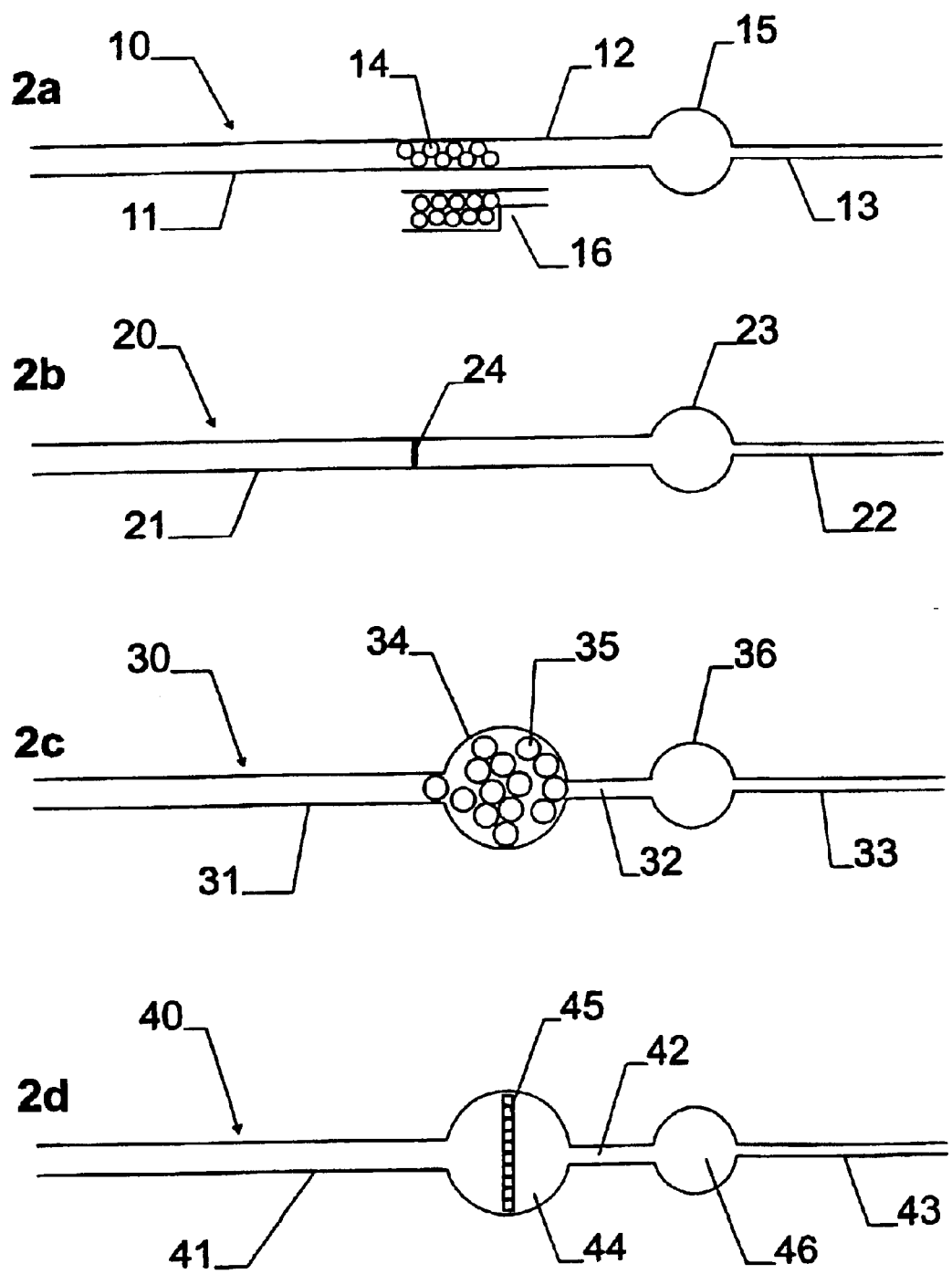
FIG. 2a is a diagrammatic representation in plan of an individual micro-channel element of a microfabricated apparatus containing microbeads for DNA isolation.
FIG. 2b is a diagrammatic representation in plan of an individual micro-channel of a microfabricated apparatus in which the micro-channel is provided with raised structures disposed on the base portion of the micro-channel to form pillars.
FIG. 2c is a diagrammatic representation in plan of an individual micro-channel of a microfabricated apparatus in which micro-beads are contained within a chamber formed in the micro-channel.
FIG. 2d is a diagrammatic representation in plan of an individual micro-channel of a microfabricated apparatus in which raised structures are disposed within a chamber formed in the micro-channel.

The present invention provides a method for isolating DNA from cells using a microfabricated apparatus (shown in FIG. 1) comprising a rotatable disc (1) microfabricated to provide a sample introduction port (not shown) located towards the centre of the disc and connected to an annular sample reservoir (2) which in turn is connected to a plurality of radially dispersed micro-channels (3). Each of the micro-channels (3) comprises a sample inlet channel (4) and an outlet channel (5) disposed towards the circumferential edge of the disc for removal of liquid and or samples therefrom. A cover plate (not shown) is positioned onto the disc so as to define closed chambers and connecting channels. Each micro-channel is connected at one end to the annular sample reservoir (2) and at the opposite end to a common waste channel (6).

Suitably the disc (1) is of a one- or two-piece moulded construction and is formed of an optionally transparent plastic or polymeric material by means of separate mouldings which are assembled together to provide a closed structure with openings at defined positions to allow loading of the device with liquids and removal of liquid samples. Suitable plastic or polymeric materials may be selected to have hydrophobic properties. Preferred plastics or polymeric materials are selected from polystyrene and polycarbonate. In the alternative, the surface of the micro-channels may be additionally selectively modified by chemical or physical means to alter the surface properties so as to produce localised regions of hydrophobicity or hydrophilicity within the micro-channels to confer a desired property. Preferred plastics are selected from polymers with a charged surface, suitably chemically or ion-plasma treated polystyrene, polycarbonate or other rigid transparent polymers.

In its simplest form, the device is produced as two complementary parts, one or each carrying moulded structures which, when affixed together, form a plurality of micro-channels within the body of a solid disc and being radially disposed about the centre. Alternatively the micro-channels may be formed by micro-machining methods in which the micro-channels are micro-machined into the surface of a disc, and a cover plate, for example a plastic film, is adhered to the surface so as to enclose the channels.

The individual micro-channels (3) of the microfabricated apparatus are shown in FIGS. 2a–2d. In one preferred aspect (shown in FIG. 2a), each of the micro-channels (10) comprises a sample inlet channel (11) connected at its left hand end to the reservoir (2), leading through channel (12) to a reaction chamber (15) and an outlet channel (131 connected at its right-hand end to the waste channel (6). Each micro-channel contains a layer or "plug" of micro-beads (14) upstream of the reaction chamber (15) and held in place by means of a stepped wall or interface of the micro-channel (16). The "plug" of beads acts to capture DNA and cell nuclei passing through the micro-channel, while allowing the passage of liquid. Advantageously, channel (11) upstream of the interface (16) is characterised by having a larger cross-sectional area than channel (12) downstream of the interface (16). Suitably the cross-sectional area of the channel (12) downstream of the interface (16) is between 0.99 and 0.01 times that of the channel upstream of the interface and is suitably of dimensions which do not allow the passage of the microbeads, which will form a "plug" at the interface between the upstream and downstream channels.

In a second preferred aspect of the present invention (shown in FIG. 2b), each of the micro-channels (20) comprises a sample inlet channel (21) connected at its left hand end to the reservoir (2), leading through channel (12) connected to a reaction chamber (23) and an outlet channel (22) connected at its right-hand end to the waste channel (6). The channel (21) upstream of the reaction chamber (23) is provided with raised structures disposed on the base portion of the micro-channel. The raised structures are moulded to form pillars (24), such that they form a barrier to the flow or passage of DNA and cell nuclei arriving thereto, while allowing the passage of liquid.

In another preferred aspect of the invention (shown in FIG. 2c), each of the micro-channels (30) comprises an inlet channel (31) connected at its left hand end to the reservoir (2), a chamber (34) containing a plurality of microbeads (35) for use in performing the method of the invention, and connected through a channel (32) to reaction chamber (36) and an outlet channel (33), leading to the common waste channel (6). Advantageously, the channel (32) which connects chamber (34) with the reaction chamber (36) is characterised by having a cross-sectional area between 0.99 and 0.01 times that of the channel (31) upstream of the chamber (34) and is of dimensions which do not allow the passage of the microbeads, thereby causing the "plug" of beads to be concentrated in the chamber.

In a further preferred aspect of the present invention (shown in FIG. 2d), each of the micro-channels (40) comprises an inlet channel (41) connected at its left hand end to the reservoir (2), a chamber (44) connected through a channel (42) to reaction chamber (46) and an outlet channel (43), leading to the common waste channel (6). The chamber (44) may be provided with raised structures disposed on the base portion of the chamber. The raised structures are moulded to form pillars (45), such that they form a barrier to the flow or passage of cells arriving thereto, while allowing the passage of liquid.

Suitably, chambers (34, 44) are sized to give a floor area between 100 $\mu m^2$ and 4,000,000 $\mu m^2$, preferably between 1000 $\mu m^2$ and 1,000,000 $\mu m^2$ and most preferably between 10,000 $^2$ and 1,000,000 $\mu m^2$.

The micro-channels are suitably of dimensions compatible with movement of cell nuclei. Suitably, the micro-channels may be of any cross-sectional shape, such as square, rectangular, circular, trapezoid and triangular and will typically have dimensions of the order 20–30 $\mu m$ or greater. Suitably micro-channels of width 250 $\mu m$ may be used.

Preferably as shown in FIGS. 2a–2d, each of the micro-channels is provided with a reaction chamber (15, 23, 36, 46) for manipulation of the DNA or for performing assays using DNA isolated by the method of the invention, and being connected in-line downstream of the barrier. The reaction chamber is suitably between twice and one tenth of the volume of chambers (34, 44). Typically, a suitable volume of reactants for performing an assay or manipulating DNA prepared by the method of the invention is between 10 nl and 1 $\mu l$. Suitably, the outlet channels (13, 22, 33, 43) are characterised by having a cross-sectional area between 0.99 and 0.01 times that of the channels (12, 20, 32, 42) upstream of the reaction chambers (15, 23, 36, 46).

The raised structures (pillars) formed in the micro-channels (24) or chambers (45) are of dimensions chosen to provide gaps between the structures that are too narrow to allow passage of cell nuclei carried as a liquid suspension in the device, while allowing the passage of liquid. Suitable dimensions for the gaps between the raised pillars formed in the micro-channels (24) or in the chambers (45) of the apparatus are between 5 $\mu m$ and 50 $\mu m$, depending upon the cell nuclei type and size selected for capture.

Beads employed in the method of the invention may be of any suitable composition, for example plastics materials. Suitable plastics may be porous or non-porous depending upon the degree of cross-linking in the polymer and include polystyrene, styrene acrylate co-polymer, polystyrene cross-linked with divinylbenzene, polyvinyltoluene, polymethacrylate and polycarbonate. Alternative materials include polysaccharides (such as dextran), metal oxides (such as aluminium oxide), glass and carbon. Preferably the surface of the beads is of a material which is capable of binding DNA, for example by hydrophobic bonding, charge interaction, or physical adsorption. A charged surface on the beads may favour electrostatic interaction, while an uncharged polymer surface may promote hydrophobic bonding. The surface of the beads may therefore be treated or activated by chemical or physical means to improve the binding capability of DNA. For example, the surface of the beads may be derivatised or modified with positively charged chemical groups as would be known to the skilled person in order to render the surface more susceptible to binding by DNA. Binding may be further improved by application of additional coating to the surface of the beads, eg. polylysine. Bead size suitable for DNA capture is suitably between 5 $\mu m$ and 100 $\mu m$, preferably between 15 $\mu m$ and 50 $\mu m$.

The nature and source of the cells is not critical to the invention. That is, nucleated cells from any source may be used, including plant cells and animal cells. The invention is particularly useful for the isolation of cell nuclei and DNA from mammalian cells, including whole blood. The first stage of the method for isolating cell nuclei from cells is the selective lysis of the cell membrane of whole cells together with a small proportion of the nuclear membranes. This stage of the method may be performed in a suitable vessel and the cell lysate transferred to the annular sample reservoir of the microfabricated apparatus. Alternatively, a cell suspension may be introduced into the sample reservoir and the lysis buffer then added so as to lyse the cytoplasmic membranes and some of the nuclear membranes according to the method. Protocols for the lysis of cells according to the method of the invention are disclosed in U.S. Pat. No. 5,447,864. For example, a lysis buffer containing 10 mM Tris pH 8.0, 320 mM sucrose and 1% Triton X-100 may be used to lyse red cells and white cell membranes and some nuclear membranes, by incubating the cells at room temperature for 5 minutes. Alternative lysis buffers which are suitable in the method of the invention are anionic detergents such as SDS (sodium dodecyl sulphate).

The cell lysate mixture obtained as described above is introduced into the inlet channel of each of the micro-channels of the microfabricated apparatus (1) and the disc is rotated by suitable means and at a speed sufficient to cause movement of the cell lysate outward towards the periphery of the disc by centripetal force and along each of the inlet channels (4) towards the barrier of beads or pillars formed in the micro-channels of the disc. In this way, rotation of the disc causes the cell lysate to flow towards the barrier disposed in the micro-channel and to form a mesh comprising DNA for capture of further DNA, or cell nuclei. Alternatively, the cell lysate mixture may be applied as discrete droplets onto the hydrophobic surface of the stationary disc, rotation of the disc being used to move the mixture into the appropriate micro-channel for capture of DNA and cell nuclei at the barrier. The captured DNA mesh is then washed by passing a washing solution through the mesh formed in the micro-channel. The wash solution is introduced into the microfabricated apparatus via the inlet channel of each micro-channel and the disc is rotated so as to cause movement of the wash solution along the micro-channels and through the DNA mesh captured therein.

Following the wash step to remove contaminants present in the captured DNA and cell nuclei, the cell nuclei captured by the mesh are further treated to release DNA by passing a solution containing a lysis reagent through each micro-channel. The lysis reagent is one which is capable of disrupting the nuclear envelope. For example, a reagent containing 0.5% (w/v) sodium dodecyl sulphate and proteinase K (250 μg/ml) in a phosphate buffered saline solution may be used. Alternatively, the nuclear membranes of the cell nuclei captured in the DNA mesh may be disrupted by heating the disc at a temperature between 80° C. and 95° C. for 1–30 minutes.

Following release, the nuclear DNA may be removed from the barrier by washing. Processing of the DNA obtained by the method of the invention may be carried out either on the mesh, or the DNA may be moved by centripetal force towards the periphery of the microfabricated apparatus for subsequent processing. In this case, the individual micro-channels of the microfabricated apparatus may be provided with a reaction chamber disposed closer to the periphery of the disc and connected in-line in the micro-channel between the barrier means and the outlet channel. The reaction chamber is connected to the common waste channel by a narrow channel having a smaller diameter than that upstream of the reaction chamber. The difference in diameters of the channels allows, under controlled conditions of rotation and centripetal force as discussed above, samples of DNA isolated by the method of the invention to be moved from the locus of the barrier to the reaction chamber and allowing subsequent additions of reagents for processing or manipulating the DNA.

The DNA isolated by the method of the invention is suitable for PCR or other processes. If restriction of the DNA is required, then restriction digests may be carried out in-situ on the mesh. The restriction digested DNA may likewise be moved to the reaction chamber for subsequent processing, by rotating the disc at a suitable speed.

The invention is further illustrated by reference to the following examples.

EXAMPLE 1

In a specific experiment the following steps were taken in which liquids were introduced into the micro-channel by suction:

A micro-channel of the following dimensions (4000 μm long×120 μm wide with a depth of 60 μm for half the length and 10 μm for the rest of the channel) was loaded with a small volume of rigid monodisperse spherical plastic beads (polystyrene cross-linked with underivatised divinylbenzene, SOURCE™ particles, Amersham Pharmacia Biotech) with a diameter of 15 μm. These formed a thin layer of beads at the interface between the deep and shallow regions of the micro-channel (see FIG. 2a).

5 μl of whole EDTA blood were mixed with an equal volume of Lysis Buffer containing 10 mM Tris pH 8.0, 320 mM sucrose, 5 mM $MgCl_2$ and 1% (v/v) Triton X-100, and incubated at room temperature for 5 minutes. The lysate was diluted ten-fold with a 1:1 mixture of Lysis Buffer and Phosphate Buffered Saline (PBS, Sigma). A volume of 0.4 μl of the diluted lysate was drawn through the micro-channel containing the beads. The beads were washed with 1 μl of PBS followed by 1 μl of a 1:200 dilution of PicoGreen (a specific fluorescent stain for double-stranded DNA; Molecular Probes Inc., USA) in TE (10 mM Tris/HCl, 1 mM EDTA, pH 7.5), followed by 1 μl of TE only.

Figure 3:
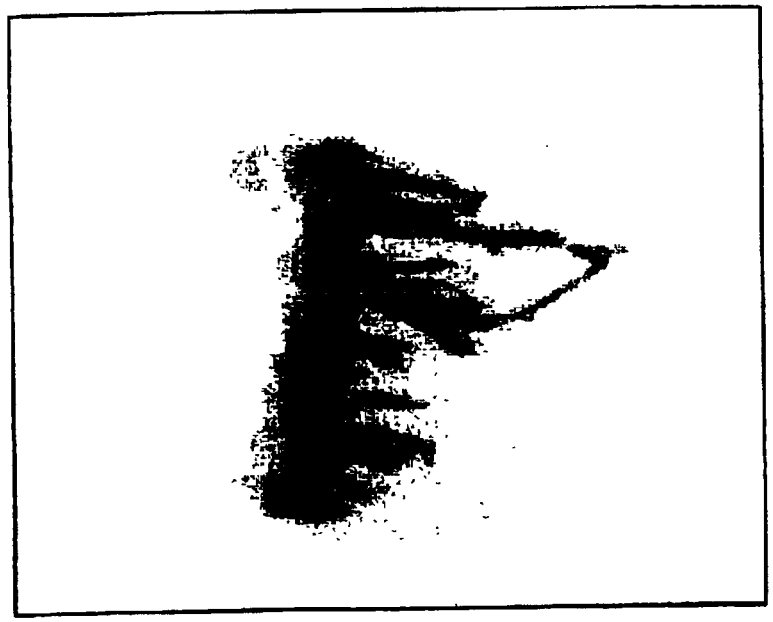
FIG. 3 is an image showing DNA from whole human blood with EDTA as anticoagulant captured with beads according to the method of the invention and visualised with PicoGreen stain using an epifluorescence microscope; and, FIG. 4 is an image from a control sample in which PBS buffer was passed through the micro-channel according to the method.
Figure 4:
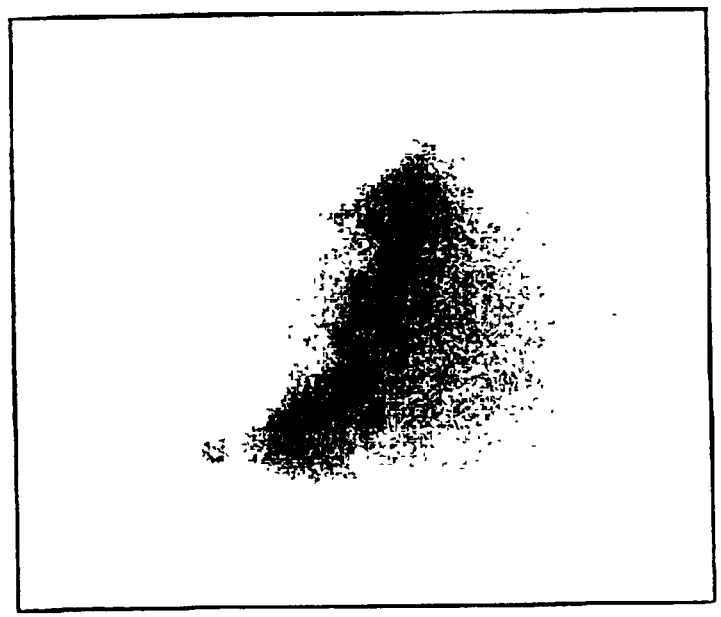

The beads were examined using an epifluorescence microscope with an activation wavelength of approximately 480 nm and emission wavelength of approximately 520 nm to visualise the PicoGreen stain bound to the DNA on the beads (shown in FIG. 3). Controls, in which PBS substituted the blood, were run through the same process giving only background fluorescence of the beads packed at the interface between deep and shallow sections of the micro-channel (shown in FIG. 4).

EXAMPLE 2

DNA was isolated from frozen citrate blood on a shallow bead bed as in described in Example 1 except that it was not visualised with PicoGreen. In this case a somewhat larger channel was used (4000 μm long×650 μm wide with a depth of 55 μm for half the length and 10 μm for the rest of the channel).

A solution containing the following reagents was introduced into the chamber to lyse the nuclei and release the DNA: 10 mM Tris/HCl, pH 8; 0.5% SDS; 1 mg/ml Proteinase K. The reaction mixture was incubated at 55° C. for 5 minutes. The contents of the chamber were washed out with 1 μl of a solution containing the following components: 1×PCR Buffer II (Perkin Elmer ABI); 6% (w/v) α-cyclodextrin (Aldrich). The resulting liquid was collected and diluted to 10 μl with water.

PCR was run on the extracted DNA as follows:

Five microlitres of diluted DNA were added to a PCR mixture (final volume 25 μl) containing the following components: 1×PCR buffer II (Perkin Elmer ABI); 1.5 mM $MgCl_2$; 200 μM deoxynucleotides; 1 U AmpliTaq Gold (Perkin Elmer ABI); 15 pmol of each primer specific for a 1035 bp region of the CYP2D6 gene covering exon 2 and part of the flanking introns. The reaction mixture was cycled using the following protocol: 95° C.×9 min; (95° C.×15 s, 60° C.×30 s, 72° C.×45 s)×35; 72° C.×5 min.

Products were analysed by agarose gel electrophoresis and staining with ethidium bromide followed by visualisation under UV light. Clearly visible PCR products were obtained from the test DNA. Product was absent in negative controls and present in positive controls containing pure DNA isolated by another method.

The PCR products were diluted 1:1000 and 2.5 μl of this diluted template were added to a second PCR mixture (final volume 25 μl) containing the same components as the first excepting the primers which covered a 262 bp region including exon 2 of CYP2D6, and AmpliTaq was used. The cycle program was the same with the omission of the initial incubation at 95° C. required only when using AmpliTaq Gold. Similar reactions were done using 1 μl of the original diluted DNA isolate (i.e. non-nested amplification of the original DNA was attempted).

Agarose electrophoresis again indicated the presence of PCR products generated from the isolated DNA. In this case, the nested PCR gave very strong amplification. Week but clearly visible products were also obtained when using the original DNA directly in the PCR. Negative and positive controls gave expected results.

What is claimed is:

1. A method of isolating DNA and/or cell nuclei in a microfabricated apparatus that contains a plurality of radially dispersed micro-channels the method comprising forming a mesh from a cell sample in one or more of the micro-channels which mesh acts as a barrier to DNA and/or cell nuclei.

2. The method according to claim 1 wherein the mesh formed in the said one or more micro-channels of the microfabricated apparatus comprises a mesh of nucleic acid.

3. A method of isolating DNA or cell nuclei or a mixture thereof from cells, which method comprises:
   a) treating a suspension of whole cells with a lysis reagent so as to lyse the cytoplasmic membranes and at least some of the nuclear membranes;
   b) introducing the lysate from step a) into micro-channels of a microfabricated apparatus wherein each of said micro-channels incorporates means to impede the passage or flow of DNA and cell nuclei while allowing the passage of liquid through the micro-channel whereby a mesh comprising DNA is formed in the channel; and,
   c) washing the mesh comprising DNA.

4. The method according to claim 3 wherein the step a) a proportion of the nuclear membranes is left intact.

5. The method according to claim 3, wherein the microfabricated apparatus comprises a rotatable disc, the disc comprising a sample introduction port located towards the center of the disc in contact with an annular sample reservoir which in turn is connected to a plurality of radially dispersed micro-channels, each micro-channel comprising an inlet channel and an outlet channel disposed towards the circumferential edge of the disc and means incorporated in each of the micro-channels to impede the passage or flow of DNA and cell nuclei, while allowing the passage of liquid therethrough.

6. The method according to claim 3, wherein said means incorporated in each of the micro-channels to impede the passage or flow of DNA and cell nuclei comprises a barrier.

7. The method according to claim 6 wherein said barrier comprises beads that impede the flow or passage of DNA and cell nuclei in the micro-channel while allowing the passage of liquid.

8. The method according to claim 7 wherein said beads are selected from the group consisting of polystyrene beads, styrene acrylate co-polymer beads, polystyrene cross-linked with divinylbenzene beads, polyvinyltoluene beads, polymethacrylate beads, polycarbonate beads, polysaccharide beads, metal oxides beads, glass beads and carbon beads.

9. The method according to claim 6 wherein said barrier comprises raised structures disposed in the micro-channel.

10. The method according to claim 9 wherein said raised structures are disposed on the base portion of the micro-channel and are moulded to form pillars such that they impede the flow or passage of DNA and cell nuclei in the micro-channel while allowing the passage of liquid.

11. The method according to claim 3, wherein at least some of the micro-channels of the microfabricated apparatus each further comprise a reaction chamber for performing assays or processing DNA.

12. The method according to claim 3, wherein the whole cells of step a) are selected from plant cells and animal cells.

13. The method according to claim 3, wherein step c) is performed by passing a washing solution through the mesh formed in the micro-channel.

14. The method according to claim 3, wherein cell nuclei captured by the mesh are further treated to release DNA.

15. A microfabricated apparatus for isolating DNA or cell nuclei or a mixture thereof from cells, which apparatus comprises a rotatable disc, the disc comprising a sample introduction port located towards the center of the disc in contact with an annular sample reservoir which in turn is connected to a plurality of radially dispersed micro-channels, each micro-channel comprising an inlet channel and an outlet channel disposed towards the circumferential edge of the disc and a barrier disposed in each of the micro-channels to impede the passage or flow of DNA and cell nuclei, while allowing the passage of liquid there through, said barrier being selected from beads or raised structures.

16. The apparatus according to claim 15 wherein said raised structures are disposed on the base portion of the micro-channel and are moulded to form pillars.

* * * * *